US008962046B2

(12) United States Patent
Mälkki

(10) Patent No.: US 8,962,046 B2
(45) Date of Patent: Feb. 24, 2015

(54) SATIETY INDUCING PRODUCTS AND A METHOD OF THEIR PRODUCTION

(75) Inventor: Yrjö Mälkki, Espoo (FI)

(73) Assignee: Teknologian Tutkimuskeskus VTT, VTT (FI)

( * ) Notice: Subject to any disclaimer, the term of this patent is extended or adjusted under 35 U.S.C. 154(b) by 875 days.

(21) Appl. No.: 12/440,230

(22) PCT Filed: Sep. 6, 2007

(86) PCT No.: PCT/FI2007/000223
§ 371 (c)(1),
(2), (4) Date: Mar. 5, 2009

(87) PCT Pub. No.: WO2008/028994
PCT Pub. Date: Mar. 13, 2008

(65) Prior Publication Data
US 2009/0281039 A1      Nov. 12, 2009

(30) Foreign Application Priority Data

Sep. 6, 2006  (FI) ...................................... 20060795

(51) Int. Cl.
*A61K 36/00* (2006.01)
*A61K 36/8998* (2006.01)
*A23L 1/29* (2006.01)
*A23L 1/05* (2006.01)
*A23L 1/10* (2006.01)
*A23L 1/30* (2006.01)
*A23L 1/308* (2006.01)

(52) U.S. Cl.
CPC . *A23L 1/293* (2013.01); *A23L 1/05* (2013.01); *A23L 1/1016* (2013.01); *A23L 1/3006* (2013.01); *A23L 1/308* (2013.01); *A23V 2002/00* (2013.01)
USPC .......................................... 424/726; 424/750

(58) Field of Classification Search
None
See application file for complete search history.

(56) References Cited

U.S. PATENT DOCUMENTS

| | | | |
|---|---|---|---|
| 5,104,677 | A | 4/1992 | Behr et al. |
| 7,030,092 | B1 | 4/2006 | Levine |
| 2002/0012733 | A1* | 1/2002 | Kester et al. ................... 426/549 |
| 2003/0008810 | A1* | 1/2003 | Portman ........................... 514/2 |
| 2003/0013679 | A1 | 1/2003 | Wolf et al. |
| 2004/0096479 | A1 | 5/2004 | Levine |
| 2004/0219261 | A1* | 11/2004 | Triantafyllou Oste et al. . 426/49 |
| 2005/0084549 | A1* | 4/2005 | Pilgaonkar et al. ............ 424/757 |
| 2005/0255126 | A1* | 11/2005 | Tsubaki et al. ........... 424/195.16 |
| 2006/0099324 | A1* | 5/2006 | Aurio et al. ................... 426/656 |
| 2006/0141101 | A1 | 6/2006 | Chen et al. |
| 2006/0165758 | A1 | 7/2006 | Wolf et al. |

FOREIGN PATENT DOCUMENTS

| | | |
|---|---|---|
| JP | 61-115465 A | 6/1986 |
| JP | 2005-46054 A | 2/2005 |
| WO | WO-99/02041 A1 | 1/1999 |
| WO | WO-01/26479 A1 | 4/2001 |
| WO | WO-02/47614 A2 | 6/2002 |
| WO | WO-02/090527 A1 | 11/2002 |
| WO | WO-03/004044 A1 | 1/2003 |
| WO | WO-2006/124929 A2 | 11/2006 |

OTHER PUBLICATIONS

Ruzaidi et al, The effect of Malaysian cocoa extract on glucose levels and lipid profiles in diabetic rats, Journal of ethnopharmacology, (Apr. 8, 2005) vol. 98, No. 1-2, pp. 55-60.*
Masclee, A. et al. "Placebo controlled study on the effect of soluble fibre and fat on satiety." Gastroenterology, 1997, vol. 112, No. 4 suppl., p. A891.
Konuklar, G. et al., "Use of a Beta-glucan hydrocolloidal suspension in the manufacture of low-fat Cheddar cheeses: textural properties by instrumental methods and sensory panels." Food Hydrocolloids, 2004, vol. 18, pp. 535-545.
Anttila et al., "Viscosity of beta-glucan in oat products." Agricultural and food science, 2004, vol. 13, pp. 80-87.
French et al., "Effect of guar gum on hunger and satiety after meals of differing fat content: relationship with gastric emptying." The American Journal of Clinical Nutrition, 1994, vol. 59, pp. 87-91.
Britt Burton-Freeman, "Dietary Fiber and Energy Regulations." The Journal of Nutrition, 2000, vol. 130, pp. 272S-275S.
Mattes et al., "Beverage viscosity is inversely related to postprandial hunger in humans." Physiology & Behavior, vol. 74, 2001, pp. 551-557.
Howarth et al., "Nutrition Reviews" vol. 59, May 2001, pp. 129-139.
Juvonen et al., "Postprandial Responses of Bulking and Viscosity-Producing Cereal Fibers." p. 33, 2006.
Marciani et al., "Gastric Response to Increased Meal Viscosity Assessed by Echo-Planar Magnetic Resonance Imaging in Humans." American Society for Nutritional Sciences, 2000, pp. 122-127.
Roberts et al., "The Influence of Dietary Composition on Energy Intake and Body Weight." Journal of the American College of Nutrition, vol. 21, No. 2, pp. 140S-145S, 2002.
Rothacker, Dana et al., "Short-term hunger intensity changes following ingestion of a meal replacement bar for weight control", International Journal of Food Sciences and Nutrition, vol. 5, No. 3, 2004, pp. 223-226.
Juvonen et al., "Postprandial Responses of Bulking and Viscosity-Producing Cereal Fibers", Workshop Neuroendocrinological Regulation of Food Intake, Kuopio University, p. 33 (2006).

* cited by examiner

*Primary Examiner* — Qiuwen Mi
(74) *Attorney, Agent, or Firm* — Birch, Stewart, Kolasch & Birch, LLP

(57) ABSTRACT

The invention relates to a food product inducing satiety with the aim of contributing to weight management. The product contains as its essential ingredients viscous soluble dietary fiber or other thickening agent and fat or fatty acids. A preferred component contained in the product is a barley or oat bran concentrate rich in β-glucan. The product may have a pasty consistency, or it may have a particulate consistency and can be turned to a paste by addition of water.

25 Claims, No Drawings

SATIETY INDUCING PRODUCTS AND A METHOD OF THEIR PRODUCTION

The aim of this invention is to present a product or a group of products, which when given as small doses cause in human a satiety lasting for several hours after ingestion of such products, and reduces food intake during one or several subsequent meals. It is the purpose that such products can be included in the daily diet without difficulties for weight control purposes. The products can also be used for controlling contents of cholesterol, glucose and insulin in blood. Furthermore, the aim is to present a method for their production.

Obesity and overweight have during the last decennia become one of the largest public health problems internationally. According to the statistics of World Health Organization (WHO), globally the amount of persons with overweight (body weight index greater than 25 kg/m$^2$) is over one billion, and about 30% of them are obese (body weight index greater than 30 kg/m$^2$). In many industrialized countries the amount of overweight and obese persons is about 60% of the adult population. The most important health consequences are type 2 diabetes, increased risks of coronary and heart diseases, diseases of joining and supporting organs, and some forms of cancer. For instance in the United States the estimated total mortality in various diseases where one of the causative factors is overweight or obesity, is 1000 persons daily. Chemotherapeutic or surgical cure of obesity is used only in extreme cases. The most commonly recommended treatment is a low-energy diet and an increase of physical exercise.

For dietary treatment of overweight and obesity, a great variety of commercial low-energy preparations are available, but related to the need, their use has been insufficient. This is mainly due to the price level of these preparations, a continuous daily dependence of commercial or home-made low-energy meals, separate preparation of meals for the dieter and for other family members, discontinuities caused by these factors or due to unsatisfactory sensory properties of the diet foods, getting tired to the limited variation of such foods, or of losing motivation to the dieting.

Satiety and food intake are controlled on one hand by signals of need of energy, on the other by physical, hormonal and palatability signals connected with the intake of food. Dietary fibre received from the diet affects this control as well directly due to its physical properties in the stomach and small intestine, as indirectly by affecting the secretion or formation of hormones or mediators in the intestinal tract or hormone secreting glands. Especially the roles of ghrelin, cholecystokinin and glucagon-like peptide 1 (GLP-1) are regarded central in this control. Ghrelin, which is secreted mainly by special secreting cells of the epithelium of stomach, is a hormone increasing appetite. Cholecystokinin and GLP-1 are both secreted in the small intestine and have both appetite-reducing effects. Fat and fatty acids have been found to reduce the secretion of ghrelin and increase the secretion of cholecystokinin and GLP-1. Despite the above, knowingly only two products based on the effects of fats or fatty acids, Fabuless™ by DSM, The Netherlands, and PinnoThin™ by Lipid Nutrition, The Netherlands, have been so far marketed. For both of these, effects on satiety and release of intestinal hormones have been published, but no publications exist so far on a weight reducing effect.

The satiety-inducing effect of dietary fibre has been until now regarded to be caused in part by its ability to bind water and cause volume increase in the stomach. This swelling causing distension in the stomach gives via the nervous system a signal to the brain. Increases of both volume and viscosity in the stomach retard the gastric emptying. Increase of viscosity retards the absorption of nutrients in the small intestine. However, the daily amount of dietary fibre needed for weight reduction without limiting the food intake otherwise is high. According to the review of Howarth et al. (Nutrition Reviews 59 (2001), 129-139), an addition in daily intake of dietary fibre by 14 g has effected, as a mean of several studies, a decrease of 1.9 kg during 3.8 months. An addition of this magnitude is, however, unrealistic to be followed continuously. The studies included in this review did not show any difference in the efficiency of soluble and insoluble fibre. The effect of viscous soluble fibre was not specifically studied.

Fat containing meals have commonly been known to cause a slower gastric emptying than meals having a lower fat content, and thus induce a satiety of longer duration. The satiety effect of fat is however weaker than that of protein or carbohydrate diet. A diet having a low fat and low energy content leads however often to a chronic hunger feeling. This is assumed to be caused at least in part by a lower fat content in the small intestine (Burton-Freeman, Journal of Nutrition 130 (2000), 272S-275S). In comparing the satiety effects of different fatty acids, those with low chain length ($\leq C_{12}$) are commonly regarded as non-effective, but research data regarding differences in effects of fatty acids with a higher chain length or on the role of mono- or polyunsaturated acids on the satiety and energy intake are controversial.

There are only a few published studies on combined effects of fat and dietary fibre. Since especially the viscous dietary fibre reduces absorption of fat, it has been proposed, that this retardation could cause a satiety inducing effect of longer duration. In their review on intervention studies Roberts et al. (Journal of the American College of Nutrition 21 (2000), 140S-145S) have presented, that in studies shorter than one year, with diets based on reduction of fat a weight reduction of less than 1 kg, with diets based on addition of dietary fibre a mean reduction of 1.9 kg, but with diets where both fat was reduced and fibre was added, the mean reduction was 3.4 kg.

In the study of French and Read (American Journal of Clinical Nutrition 59 (1994), an addition of 12 g of guar gum in 400 ml of a soup containing 24.9 g of fat retarded gastric emptying and return of hunger, as compared to control soups with or without fat. Return of hunger was however recorded already 100 minutes after the meal. The amount of guar gum used in this study was approaching the upper level of sensorial acceptability, which for instance in bread is regarded to be 5 g/100 g.

In the study of Burton-Freeman cited above, addition of fibre causing an ample increase of viscosity into a low-fat (<20% of energy from fat) diet led to a weakening of hunger feeling and an increase of satiety, as compared to diet with a similar energy and fat content. Addition of fibre also caused an increase of cholecystokinin levels. In all of these studies, however, the fat and dietary fibre contents have been high for weight control purposes, and the diets have been composed of several ingredients.

In a study of Juvonen et al. (Workshop Neuroendocrinological regulation of food intake, Kuopio University 2006, Abstracts p. 33), effects of soluble or insoluble fibre or their combination on satiety and blood ghrelin content were investigated. Test meals were puddings and had a total energy content of 1250 kJ. The total amount of fibre was varied between 1.6 to 10.6 g. that of viscous soluble fibre from 0 to 5.1 g., and the fat content was 3.7%. No significant differences in the effects on satiety or blood ghrelin content were found. Ghrelin secretion started to return two hours after the meal.

The energy content of meal replacement preparations is usually in the order of 800 to 1100 kJ/serving. The products are usually in liquid state, or products marketed in solid state are intended to be consumed in liquid state. Of the products listed in U.S. Pat. Nos. 7,030,092 and 7,067,498 and intended for diabetic patients or for weight control, more than a half had a fat content of 35% or more of the total energy content, and the fat contained principally unsaturated fatty acids. Since the target in the meal replacement products is to cover completely or nearly completely the daily need of the various nutrients in a balanced way, the amount and composition of fat is planned accordingly, and no experimental results nor other indications or motivations of any combined effects of fat and dietary fibre on satiety have been presented in these connections. A part of the products listed contained also viscous soluble fibre. The viscosity of a drink product when consumed is according to U.S. Pat. No. 7,067,498 below 300 cps.

Viscosity of liquid meal replacers has been found to affect satiety and food intake on the subsequent meal, but surprisingly little. In the study of Mattes and Rothacker (Physiology and Behavior 74 (2001) 551-557) two products with a similar energy content (924 kJ) and fat content (3 g), but differing viscosities (600 and 16000 cps) were compared. The weakening of hunger feeling and its return to the starting level were surprisingly similar, although differed statistically significantly, but there was no significant difference in the food intake during the following meal nor during the following 24 hours. Return of hunger occurred with the low-viscosity product within 4 hours, with the high-viscosity product within about 4.5 hours. The liquid volume of the meals was 325 ml.

A product which had a nearly similar energy content (1050 kJ) but a higher fat content (8 g), which was in solid state and had 4 g dietary fibre per single dose gave a satiety lasting for 5 hours as a mean (Rothacker and Watemberg, International Journal of Food Science and Nutrition 55 (2004) 223-226). The amount of water taken during the test and the follow-up time of 6 hours was limited to one glass, not given precisely. No data on the composition nor viscosity properties of the fibre have been given. During a testing period of six weeks the experimental subjects replaced daily 1 to 2 meals with this product. A mean weight reduction of men was $5\pm2.9$ kg, of women $3.4\pm2.2$ kg.

The purpose of this invention has been to create a product or group of products, which can as such or after a short preparation be consumed as a part of an ordinary meal. The main functional goal has been, that the product reduces the appetite sufficiently to reduce the daily food energy intake when following a conventional dietary pattern. Furthermore, the product should be in regard to its sensory properties acceptable for the consumer for a daily use. Another purpose has been to develop methods for industrial preparation of these products.

The invention and a number of embodiments of the same are defined in the appended claims 1-26.

In the research now performed it has been surprisingly observed, that ingesting a food product having a high content of viscous soluble dietary fibre simultaneously with a food component containing fat or free fatty acids causes a rapidly developing feeling of satiety, which continues intensively at least three hours after the test meal, and depending of the dose and viscosity properties can last even for 12 hours and have posterior effects also the following day. The feeling of satiety includes a sense of a slow gastric emptying, and consequently the appetite on the following meals is weaker than usually.

The rapidity of the effect indicates that the effect starts already in the stomach and/or in the upper part of the small intestine. Without being bound to any hypothesis of a mechanism, the following explanation seems probable. As it is known regarding the flow properties of liquids in general, viscosity increases the thickness of stationary and laminar flow layers adjacent to surfaces. In the stomach, an increase of viscosity is counteracted by rapid dilution and mixing, minimizing the delay of gastric emptying (Marciani and collaborators (Journal of Nutrition 130 (2000), 122-127). A high viscosity of the food ingested allows a part of the gastric content to remain adjacent to the epithelial cells and thus prolong the contact of fat or fatty acids to the ghrelin secreting cells. In the small intestine the viscosity is lower than in the stomach due to dilution effects, but laminary flow layers exist due to the slower flow rate. Thus a similar prolonged contact with the secreting cells is possible also in the small intestine regarding secretion of cholecystokinin, GLP-1 and possibly other satiety affecting intestinal hormones or mediators. These effects evidently are additive to the effects of the volume increase due to the hydration of fibre. The retarded gastric emptying also retards the hydrolysis of starch to glucose and its absorption in the small intestine, which has an advantageous effect on the control of blood glucose and insulin. An additional benefit is the known effect of viscous soluble fibre on blood cholesterol.

A high viscosity in the upper part of the intestinal tract can be advantageously achieved by ingesting a readily hydrated product in a concentrated state, however within sensorially acceptable limits. A possible way is to swell a mixture of dry ingredients to a pasty consistency and use this paste as a sandwich spread, salad dressing, or sauce for warm dishes. Such preparation can be made microbiologically stable using heat treatments such as pasteurisation, high-temperature-short-time sterilization or conventional sterilization, whereby also residual enzyme activities are inactivated. Another possible way is to prepare a powderous or granulated composition which hydrates rapidly, within less than 15 minutes to a pasty consistency. The dry preparation is suspended in a small amount of water and ingested before the swelling causes sticking in the mouth or difficulties in swallowing. For safety reasons, marketing of rapidly hydrating fibres as tablets, biscuits, candies or similar products has to be avoided and regarding tablets and candies is in many countries prohibited.

The viscous soluble fibre component can be selected, for instance, from cereal fractions containing $\beta$-glucan, or from the group guar gum, psyllium fibre, locust bean gum, cellulose derivatives, chitosan, microbiologically produced polysaccharides, or other ingredients giving high viscosities and being acceptable for food use. The effective dose depends on the viscosity properties of the ingredient. For instance, when oat bran concentrates have been used, the improved satiating effect has been advantageously achieved with a single daily dose corresponding 0.7 to 2.0 g of beta-glucan, combined with a suitable fat or fatty acid component. The product of the invention may be prepared and packed as units comprising a suitable single or daily dose, or a package may have instructions for such dosing. When suspended in 50 ml of water and optionally heat treated, the viscosity of the mixture at 25° C., as measured at a speed of 0.3 rev/min, is at least 20,000 cps, preferentially in the range 100,000 to 1,500,000 cps. These viscosities are applicable also when other viscous ingredients are used.

When preparing a product containing $\beta$-glucan it has to be observed, that the viscosity of a readily hydrated suspension can be reduced under processing or storage due to acid or enzymatic hydrolysis of the macromolecules, breakage due to shear forces or thermal effects, or structural reordering of the macromolecules during storage. Enzymatic hydrolysis can be caused by residual $\beta$-glucanase activity from the ingredients or from contaminating microorganisms. When preparing dry products, a rapid and complete solubility is of utmost importance for achieving the desired viscosity on time.

The satiating effect of a hydrated composition can also be reduced during the storage by gelling of other components of the composition, such as starch and proteins. The gel formed might enclose the viscous components and thus prevent formation of the said stationary and laminar flow layers. The effects of gelling and of structural reordering of the viscosity-forming fibre component can be counteracted, for instance, by melting the gel before use, by partial hydrolysis of carbohydrates and protein, by adding partially hydrolyzed carbohydrates or proteins, or by addition of osmotically active or amphoteric components.

For the fat component, it is advantageous to use edible fats of long-chain ($\geq C_{16}$) fatty acids, preferably containing a substantial amount, at least 50% by weight, of saturated fatty acids. Addition of fats is most advantageous when emulsified or otherwise in small-sized droplets or crystals. Addition of free fatty acids or fats being partially hydrolyzed is more effective in improving the satiety than unhydrolyzed fats. Hydrolysis of fat can be combined with hydrolysis of carbohydrates and protein when this is needed for preventing gel formation or structural reordering of the viscous component.

The amount of fat, hydrolyzed fat, fatty acids or a mixture of these needed for improving the satiety inducing effect of viscosity forming compounds is at least 0.2 grams per single dose ingested, preferably in the range 1 to 8 grams.

Implementation of the invention is described in the following examples. To ensure the reproducibility of satiety tests and enable effects of various compositional and processing parameters to be observed, results of testing by only one person having a body mass index of 21.5 kg/m² were used. Reliability of this testing was ensured by repeated tests and by observing differences caused by factors affecting the viscosity or the fat or fatty acid content on satiety and its duration, which followed the expected results in all of the more than one hundred satiety tests performed.

EXAMPLE 1

As a control test for the effect of a meal prepared to a conventional consistency, a subject having body mass index of 21.5 kg/m², took after fasting overnight a meal consisting of oatmeal porridge, strawberry jam, low-fat milk, bread, cottage cheese and coffee, with total energy content of 1,734 kJ. The fat content of the meal was 8.1 g, of which milk fat 4.0 g, and the calculated content of β-glucan was 2.16 g. The meal gave a feeling of satiety for two hours, and the first sensation of hunger was observed 3 hours after the meal.

EXAMPLE 2

Suspensions were prepared from native or cooking extruded oat bran concentrates containing 17% (extruded) or 19% (native) of β-glucan (Raisio, Finland) by mixing them in water, low-fat milk of 1.5% fat content, in food cream of 15% fat content, (Valio Oy, Finland, the preparation containing guar gum as a stabilising ingredient), or in an emulsion of partially hydrogenated palm oil with a fat content of 7% (Pirkka, Kesko Oy, Finland, the preparation containing guar gum as a stabilising ingredient). The proportions were adjusted to contain amounts of fat and fibre given in Table 1. Milk, cream and palm oil emulsion had been homogenized. After 10 minutes of swelling, the temperature was elevated to 80° C. to improve the solubilization of β-glucan, after which the batches were stored in refrigerator until testing. A part of the batches were after suspending sterilized at 121° C. for 15 minutes.

The effect on satiety was tested in experimental breakfast meals, where the amount of the suspension to be tested was 55 to 60 ml, and it was used as a spread on wholegrain wheat bread having fresh weight of 60 g. The meal also included 300 ml of coffee. Total energy content of the meal was 932 kJ, of which the bread and coffee made 690 kJ. A control meal was included containing a suspension of oat bran concentrate without added fat, wholemeal wheat bread; another control containing wholemeal bread and low-fat cottage cheese, both controls adjusted to the same total energy content as the test meals. Satiety was followed using the visual analogy method described in the publication of Cardello et al. (Appetite 44 (2005) 1-13), during 5.25 hours after ending the test meal. Results calculated from the evaluations are presented in Table 1.

According to the results, additions to β-glucan containing suspensions of milk fat, where the share of saturated acids is 58%, or partially hydrogenated palm oil, where the share of saturated fatty acids is 50%, has increased their satiating effect. When using a rapidly dissolving extruded oat bran concentrate, a distinct dose-response effect is observed regarding as well the amount of β-glucan as the amount of fat. Sterilization of preparations made from native finely milled oat bran concentrate gave higher satiety responses than pasteurised samples made from extruded concentrates. The satiating effect was gradually reduced in storage, already after a week at room temperature, but was to a great part recovered by heating to melt the gel.

As compared to Example 1, in the samples giving elevated satiety effect, both β-glucan and fat content as well as the total energy content of the test meal have been lower. The principal difference in the experimental conditions has been the more complete dissolving of β-glucan, which has resulted in a pasty consistency of the semisolid component of the test meal.

EXAMPLE 3

To study possibilities for using fat containing dry ingredients for the purpose, suspensions resembling those of Example 2 were prepared by mixing into the oat bran concentrate cocoa powder (van Houten, Lebbeke-Wieze, The Netherlands) containing 21% of fat, whereof the share of saturated fatty acids was 60%, and dietary fibre 34%, whereof 7.6 percentage units was soluble fibre; or finely milled coconut flakes (Green Taste Oy, Helsinki) containing 64.5% fat whereof the share of saturated fatty acids was 90%, or dry cheese powder (Grozette B. V., Weerden, The Netherlands) containing 28% of fat, whereof the share of saturated fatty acids was 50%. The amounts added were calculated to give contents of fat and β-glucan as given in Table 1. From a part of the mixtures, suspensions were made as in Example 2. Another part was prepared to granules of 1 to 2 mm by adding to 11 g of the dry mixture 7 ml of water, kneading it to a moist granulate and drying the granules in a microwave oven. The granulate was tested by adding 50 ml of cold water, allowing to swell at room temperature for 15 minutes, and heating the mixture to 80° C. to improve the solubility of β-glucan. Satiating effects of these mixtures were tested as in Example 2. Results are presented in Table 1.

According to the results, a satiating effect is achieved also by using these ingredients and prepared to dry products, however provided that the solubility and viscosity properties of β-glucan have not been reduced under granulating and drying operations. Increasing the fat dose to higher than 0.59 g has not improved the satiating effect. Fat from cocoa powder has been more effective than milk fat.

EXAMPLE 4

3 g of cocoa powder was mixed in 150 ml of 10 mM sodium phosphate buffer of pH 6.9. 200 mg of granulated pancreatin (creon, Solvay Pharmaceuticals GmbH, Hannover, Germany), was added. The pancreatin preparation was declared to contain 42,550 PhE units of lipase, 34,000 units of amylase, and 2,550 units of protease in a gram of granules. The mixture was incubated at 37° C. for 140 minutes. After standing for 12 hours at room temperature, 7.5 g of cooking extruded oat bran concentrate was mixed into 50 ml of the hydrolysate, this mixture was heated to 50° C. and used as sandwich spread for a test breakfast according to Example 2. Results indicating the satiating effect are presented in Table 1 and show, that 0.21 g of partially hydrolyzed cocoa fat, when combined with oat bran concentrate, has given a similar satiating effect as 0.59 g of unhydrolysed cocoa fat. A satiating effect was still observed during the subsequent lunch and dinner reducing the food intake during these meals.

EXAMPLE 5

In a part of the test meals of Example 2, the follow-up of the satiety was continued in a second test meal following the 5.25 hours control period. This meal consisted of an openly served pasta and minced meat dish and 120 g of low-fat (1.5%) milk. The amount of the pasta dish taken by the test subject was controlled afterwards by weighing. During a control meal, the total energy taken was 1,878 kJ. In a similar test lunch meal after having a test breakfast containing extruded oat bran concentrate and partially hydrogenated palm oil, the total energy intake at the lunch was 1,548 kJ.

EXAMPLE 6

50 g of beef fat was melted, mixed with 0.1 g of distilled glyceryl monostearate (Grindsted, Denmark) and emulsified in 400 ml of 0.15 M sodium acetate buffer of pH 7.2. After cooling to 37° C., 1 g of granulated pancreatin (creon, Solvay, Germany), previously ground in a mortar, was mixed to the emulsion which was then hydrolyzed at 38±1° C. for 2 hours. 23 ml of the hydrolyzed emulsion was mixed with 27 ml of water, 7.4 g of native oat bran concentrate containing 19% of β-glucan (Raisio, Finland) was added, the mixture was heated in a microwave oven with a nominal effect of 360 W for 45 sec+15 sec to boiling point, and allowed to stand at room temperature overnight. Satiating effect was tested as in Example 2 the following morning and from a duplicate sample 5 days after preparation. A third preparation was made from the same hydrolysate adding to the mixture of emulsion, water, and oat bran concentrate, 0.25 g of betain (Betafin BF 20, Danisco, Finland) as an osmotically active and amphoteric component. The results are presented in Table 1.

The results indicate that an improved satiety effect can be achieved by adding hydrolyzed beef fat to native oat bran concentrate, and the effect has been slightly improved by a short storage at room temperature, probably due to a more effective dissolving of β-glucan. Addition of betain has further improved the effect, most probably by preventing gelling of starch derived from the ingredients and/or by retarding aging-related restructuring of β-glucan macromolecules.

EXAMPLE 7

For streamlining the operations and for preventing gelling of starch and protein components deriving from the ingredients, enzymatic hydrolysis was performed simultaneously for all of the main components. The following compositional alternatives were tested: a) 7.5 g of native finely milled oat bran concentrate, b) 7.5 g of native finely milled oat bran concentrate, 2.8 g of cocoa powder, 23 mg of acesulfam K (Sunett, Nutrinova, Frankfurt am Main, Germany), and 0.5 ml of vanilla flavouring (Danisco, France), c) 5 g of native finely milled oat bran concentrate, 2.8 g of cocoa powder, 23 mg of acesulfam K, and 0.5 ml of vanilla flavouring. Each of these compositions was separately mixed with 50 ml of 0.15 M sodium acetate buffer of pH 7.5 and 50 mg of granulated and ground pancreatin (creon, Solvay, Germany), and hydrolyzed at 38±1° C. for 30 minutes. Results of the satiating effects are presented in Table 1.

Hydrolysis of oat bran concentrate has significantly improved its satiating effect, as compared to unhydrolyzed oat bran tested in Example 2. This is evidently due to the release of free fatty acids from its lipids to an extent after which an addition of another fat-containing component is not needed unless for elevating the satiating effect or for functional or taste properties. Addition of cocoa powder to the mixture to be hydrolyzed has further improved the effect. The hydrolysis has retarded the aging-related decrease of the satiating effect. Using a lower amount of oat bran concentrate has given a more favourable consistency to the product, but a similar satiating effect and shelf-life.

TABLE 1

Satiety responses of the preparations tested in the Examples.

| Fibre source | Beta-glucan g | Fat in fibre source, g | Fat added | Amount fat added, g | Product Type | Satiety top value, % | Area below curve* | Time >60% satiety, min | Return of hunger, min |
|---|---|---|---|---|---|---|---|---|---|
| Example 2 | | | | | | | | | |
| Extruded oat bran | 1.13 | 0.83 | None | 0 | Suspension | 82 | 6600 | 174 | 315 |
| No viscous fibre | 0 | 0 | Milk fat, cottage cheese | 5 | Suspension | 74 | 4905 | 75 | 255 |
| Extruded oat bran | 1.13 | 0.83 | Milk fat, from milk | 0.75 | Suspension | 86 | 6214 | 201 | 255 |
| Extruded oat bran | 1.13 | 0.83 | Milk fat from cream | 3.5 | Suspension | 88 | 9945 | 248 | 286 |
| Extruded oat bran | 0.9 | 0.66 | Partially hydrogenated palm oil | 2.8 | Suspension | 81 | 8550 | 184 | >315 |
| Extruded oat bran | 1.36 | 1 | Partially hydrogenated palm oil | 4.2 | Suspension | 90 | 10335 | 255 | >315 |
| Native oat bran | 1.13 | 0.83 | Partially hydrogenated palm oil | 3.5 | Sterilized suspension | 88.8 | 13140 | 204 | >315 |
| Example 3 | | | | | | | | | |
| No viscous fibre | 0 | 0 | Cocoa fat | 0.6 | Suspension | 74.5 | 2813 | 94 | 215 |
| Extruded oat bran | 1.13 | 0.83 | Cocoa and milk fat | 1.35 | Suspension | 89 | 9004 | 210 | >315 |

TABLE 1-continued

Satiety responses of the preparations tested in the Examples.

| Fibre source | Beta-glucan g | Fat in fibre source, g | Fat added | Amount fat added, g | Product Type | Satiety top value, % | Area below curve* | Time >60% satiety, min | Return of hunger, min |
|---|---|---|---|---|---|---|---|---|---|
| Extruded oat bran | 1.13 | 0.83 | Cocoa fat | 0.59 | Granulates | 86 | 10575 | 277 | 310 |
| Extruded oat bran | 1.13 | 0.83 | Coconut fat | 1.29 | Suspension | 88 | 8978 | 184 | 315 |
| Extruded oat bran | 1.13 | 0.83 | Coconut fat | 2.58 | Granulates | 85 | 8171 | 220 | 315 |
| Extruded oat bran Example 4 | 1.13 | 0.83 | Milk fat from dry cheese | 0.6 | Granulates | 85 | 7553 | 184 | 258 |
| Extruded oat bran Example 6 | 1.13 | 0.83 | Hydrolyzed cocoa fat | 0.21 | Suspension | 90 | 11456 | 245 | 297 |
| Native oat bran | 1.41 | 0.74 | Hydrolyzed beef fat | 2.56 | Suspension, 13 h | 80 | 9038 | 257 | >315 |
| Native oat bran | 1.41 | 0.74 | Hydrolyzed beef fat | 2.56 | Suspension, 5 d | 84 | 10328 | 257 | >315 |
| Native oat bran Example 7. | 1.41 | 0.74 | Hydrolyzed beef fat | 2.56 | Suspension + betain, 13 h | 85 | 11520 | >315 | >315 |
| Native oat bran | 1.43 | 0.75 | None | 0 | Suspension, 13 h | 80 | 10500 | >315 | >315 |
| Native oat bran | 1.43 | 0.75 | None | 0 | Suspension, 7 d | 84 | 10553 | >315 | >315 |
| Native oat bran | 1.43 | 0.75 | Hydrolyzed cocoa fat | 0.59 | Suspension, 2 d | 88 | 12293 | >315 | >315 |
| Native oat bran | 1.43 | 0.75 | Hydrolyzed cocoa fat | 0.59 | Suspension, 8 d | 88 | 11438 | 265 | 315 |
| Native oat bran | 0.95 | 0.50 | Hydrolyzed cocoa fat | 0.59 | Suspension, 13 h | 88 | 11978 | 265 | 315 |
| Native oat bran | 0.95 | 0.50 | Hydrolyzed cocoa fat | 0.59 | Suspension, 7 d | 92 | 12953 | 262 | >315 |

*Area between the satiety curve and starting level, satiety (%) x time (min)

The invention claimed is:

1. A product inducing satiety to be used for weight management, said product comprising:
   viscous soluble dietary fiber;
   water; and
   a fatty component comprising digestible fat, partially hydrolyzed fat or fatty acids, the fat, partially hydrolyzed fat or fatty acids affecting cells secreting intestinal hormones in the stomach or the small intestine;
   wherein the viscous soluble dietary fiber is a fraction of milled plant material; and
   wherein the proportion by weight of soluble dietary fiber to fat, hydrolyzed fat and/or fatty acids is the range of 1:0.5 to 1:5 and said product having been hydrated to a pasty consistency with a viscosity of 20,000 to 1,500,000 centipoise per second, when measured at a speed of 0.3 revolutions per minute.

2. The product according to claim 1, wherein the single dose contains at least 0.7 grams of β-glucan or a corresponding amount of another viscosity forming component.

3. The product according to claim 1 or 2, wherein the viscosity forming component is a fraction of oat or barley rich in β-glucan.

4. The product according to claim 1, wherein the single dose contains at least 0.6 g of added unhydrolyzed fat or at least 0.21 g of hydrolyzed fat or free fatty acids.

5. The product according to claim 1, wherein the added fat or fatty acids are as small-sized droplets or crystals.

6. The product according to claim 5, wherein at least 50% of the fatty acids are saturated.

7. The product according to claim 5 or 6, wherein the fat is at least partially hydrolyzed, or contains added free fatty acids.

8. The product according to claim 1, where gelling of starch and protein components as well as aging-related changes in the viscosity are retarded by including osmotically active or amphoteric components.

9. The product according to claim 1, where gelling of starch and protein components as well as aging-related changes in the viscosity are retarded by partially hydrolyzing carbohydrate and/or protein ingredients, or by using partially hydrolyzed carbohydrates or proteins as components of the mixture.

10. The product according to claim 1, wherein the viscosity forming composition is in a hydrated state and is preserved by sterilization, ultrahigh temperature heating or by pasteurization.

11. The product according to claim 1, consisting of milled plant material enriched in respect of soluble dietary fiber, a fatty ingredient rich in fat and/or fatty acids, and water.

12. The product according to claim 11, consisting essentially of a milled grain fraction enriched with respect to β-glucan and an aqueous fat emulsion containing at least 5% by wt of fat and/or fatty acids.

13. The product according to claim 11 or 12, consisting essentially of a milled fraction enriched with respect to β-glucan and an aqueous fat emulsion leading to a fat content of at least 0.6 g of unhydrolyzed fat or at least 0.21 g of hydrolyzed fat or free fatty acids per single dose.

14. The product according to claim 11, wherein the milled plant material is a milled grain fraction containing at least 10% by wt of β-glucan.

15. The product according to claim 11, wherein the milled plant material is a barley or oat bran concentrate enriched in respect of β-glucan.

16. The product according to claim 11, wherein the fatty ingredient is a homogenous particulate substance containing at least 10% by wt of fat and/or fatty acids.

17. The product according to claim 16, wherein the fatty ingredient is a fine-grained powder.

18. The product according to claim 11, wherein the soluble dietary fiber is β-glucan.

19. The product according to claim 1, wherein the amount of fat, partially hydrolyzed fat, fatty acids, or a mixture of the same is in the range of 0.2 to 8 grams per single ingestable dose.

20. The product according to claim 12, wherein the aqueous fat emulsion is a food cream.

21. The product according to claim 13, wherein the aqueous fat emulsion is a food cream.

22. The product according to claim 11, wherein the milled plant material is a milled grain fraction containing at least 15% by wt of β-glucan.

23. The product according to claim 11, wherein the fatty ingredient is a homogenous particulate substance containing at least 20% by wt of fat and/or fatty acids.

24. The product according to claim 16, wherein the fatty ingredient is cocoa powder.

25. The product according to claim 1, inducing a period of time for satiety from about 3 hours to 12 hours after ingestion of the product.

* * * * *